US010292922B2

(12) United States Patent
Bernard et al.

(10) Patent No.: US 10,292,922 B2
(45) Date of Patent: May 21, 2019

(54) SILICONE-WAX DISPERSION COMPOSITIONS FOR REMOVING COSMETIC FILMS

(71) Applicant: L'OREAL, Paris (FR)

(72) Inventors: Anne-Laure Suzanne Bernard, New York, NY (US); Yang Deng, Edison, NJ (US); Alexandra Jane Elisa Farran, Dayton, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/087,115

(22) Filed: Mar. 31, 2016

(65) Prior Publication Data
US 2017/0189295 A1 Jul. 6, 2017

Related U.S. Application Data

(60) Provisional application No. 62/274,081, filed on Dec. 31, 2015.

(51) Int. Cl.
*A61K 8/58* (2006.01)
*A61K 8/03* (2006.01)
*A61K 8/06* (2006.01)
*A61K 8/31* (2006.01)
*A61Q 19/10* (2006.01)
*A61Q 1/14* (2006.01)
*A61K 8/69* (2006.01)
*A61K 8/81* (2006.01)

(52) U.S. Cl.
CPC ............... *A61K 8/585* (2013.01); *A61K 8/03* (2013.01); *A61K 8/06* (2013.01); *A61K 8/31* (2013.01); *A61K 8/69* (2013.01); *A61K 8/8117* (2013.01); *A61Q 1/14* (2013.01); *A61Q 19/10* (2013.01)

(58) Field of Classification Search
CPC ........................................................ C11D 9/36
See application file for complete search history.

(56) References Cited

U.S. PATENT DOCUMENTS

| | | |
|---|---|---|
| 2,463,264 A | 3/1949 | Graenacher et al. |
| 3,635,743 A | 1/1972 | Smith |
| 3,957,713 A | 5/1976 | Jeram et al. |
| 4,693,935 A | 9/1987 | Mazurek |
| 4,725,658 A | 2/1988 | Thayer et al. |
| 4,972,037 A | 11/1990 | Garbe et al. |
| 4,981,902 A | 1/1991 | Mitra et al. |
| 4,981,903 A | 1/1991 | Garbe et al. |
| 5,011,681 A | 4/1991 | Ciotti et al. |
| 5,061,481 A | 10/1991 | Suzuki et al. |
| 5,166,355 A | 11/1992 | Leistner et al. |
| 5,209,924 A | 5/1993 | Garbe et al. |
| 5,219,560 A | 6/1993 | Suzuki et al. |
| 5,236,986 A | 8/1993 | Sakuta |
| 5,237,071 A | 8/1993 | Leistner et al. |
| 5,262,087 A | 11/1993 | Tachibana et al. |
| 5,334,737 A | 8/1994 | Thimineur et al. |
| 5,380,455 A * | 1/1995 | Tsuda ................ A61K 8/31 510/119 |
| 5,412,004 A | 5/1995 | Tachibana et al. |
| 5,468,477 A | 11/1995 | Kumar et al. |
| 5,585,091 A | 12/1996 | Pelzer et al. |
| 5,624,663 A | 4/1997 | Deflandre et al. |
| 5,645,609 A | 7/1997 | Andrean et al. |
| 5,665,687 A * | 9/1997 | Khayat ............... A61K 8/0241 510/136 |
| 5,691,172 A | 11/1997 | Belcour et al. |
| 5,711,940 A | 1/1998 | Kuentz et al. |
| 5,811,487 A | 9/1998 | Schulz, Jr. |
| 5,837,793 A | 11/1998 | Harashima et al. |
| 5,851,517 A | 12/1998 | Mougin et al. |
| 5,972,329 A | 10/1999 | Chuang et al. |
| 6,045,782 A | 4/2000 | Krog et al. |
| 6,051,216 A | 4/2000 | Barr et al. |
| 6,093,385 A | 7/2000 | Habeck et al. |
| 6,159,455 A | 12/2000 | Habeck et al. |
| 6,191,301 B1 | 2/2001 | Habeck et al. |
| 6,225,467 B1 | 5/2001 | Esteghamatian et al. |
| 6,238,649 B1 | 5/2001 | Habeck et al. |
| 6,261,544 B1 | 7/2001 | Coury et al. |
| 6,284,233 B1 | 9/2001 | Simon et al. |
| 6,338,839 B1 | 1/2002 | Auguste et al. |
| 6,342,469 B1 | 1/2002 | Lorant |
| 6,353,076 B1 | 3/2002 | Barr et al. |

(Continued)

FOREIGN PATENT DOCUMENTS

DE 19726184 A1 12/1998
DE 19746654 A1 2/1999

(Continued)

OTHER PUBLICATIONS

Mallard Creek Polymers, "Understanding the Glass Transition Temperature," Nov. 10, 2015 [retrieved from http://www.mcpolymers.com/library/understanding-the-glasstransition-temperature, Feb. 12, 2017.
International Search Report and Written Opinion for counterpart Application No. PCT/US2016/069278, dated Mar. 13, 2017.
International Search Report and Written Opinion for counterpart Application No. PCT/US2016/069271, dated Mar. 16, 2017.
International Search Report and Written Opinion for counterpart Application No. PCT/US2016/069294, dated Mar. 4, 2017.
Co-pending U.S. Appl. No. 15/394,362, filed Dec. 30, 2016.
Non-Final Office Action for Co-pending U.S. Appl. No. 15/094,259, dated Apr. 20, 2017.

(Continued)

*Primary Examiner* — Charles I Boyer
(74) *Attorney, Agent, or Firm* — The Marbury Law Group, PLLC

(57) ABSTRACT

The disclosure relates to compositions and methods for removing cosmetic films and makeup compositions from keratinous fibers. Compositions comprise at least one low-viscosity, low-volatility silicone. Methods comprise applying the compositions to keratinous fibers.

14 Claims, No Drawings

(56) References Cited

U.S. PATENT DOCUMENTS

| | | | |
|---|---|---|---|
| 6,387,355 B2 | 5/2002 | Heidenfelder et al. | |
| 6,391,289 B2 | 5/2002 | Heidenfelder et al. | |
| 6,436,373 B1 | 8/2002 | Habeck et al. | |
| 6,451,295 B1 | 9/2002 | Cai et al. | |
| 7,311,897 B2 | 12/2007 | Ehlis et al. | |
| 7,374,771 B2 | 5/2008 | Eversheim et al. | |
| 7,470,725 B2 | 12/2008 | Schwertfeger et al. | |
| 7,582,719 B1 | 9/2009 | Tan et al. | |
| 7,879,316 B2 | 2/2011 | Ferrari et al. | |
| 8,691,202 B2 | 4/2014 | Yu et al. | |
| 2002/0001570 A1 | 1/2002 | Heidenfelder et al. | |
| 2002/0004034 A1 | 1/2002 | Heidenfelder et al. | |
| 2002/0016310 A1 | 2/2002 | Habeck et al. | |
| 2003/0026815 A1 | 2/2003 | Scott et al. | |
| 2003/0068344 A1 | 4/2003 | Ferrari et al. | |
| 2003/0091520 A1 | 5/2003 | Livoreil et al. | |
| 2003/0157047 A1* | 8/2003 | Lennon | A61K 8/06 424/70.11 |
| 2003/0158363 A1* | 8/2003 | Nakanishi | A61K 8/894 528/25 |
| 2004/0137028 A1 | 7/2004 | de la Poterie | |
| 2004/0191191 A1 | 9/2004 | Ehlis et al. | |
| 2005/0013782 A1 | 1/2005 | Goppel et al. | |
| 2005/0069564 A1 | 3/2005 | Eversheim et al. | |
| 2005/0183511 A1 | 8/2005 | Giron | |
| 2005/0239950 A1 | 10/2005 | Martin et al. | |
| 2005/0244974 A1 | 11/2005 | Garcia-Franco et al. | |
| 2005/0287088 A1* | 12/2005 | Guiramand | A61K 8/062 424/59 |
| 2006/0034875 A1 | 2/2006 | Nakanishi et al. | |
| 2006/0193801 A1* | 8/2006 | Blin | A61K 8/90 424/63 |
| 2007/0055014 A1 | 3/2007 | Lu et al. | |
| 2007/0140991 A1 | 6/2007 | Maitra et al. | |
| 2007/0224147 A1 | 9/2007 | Richard | |
| 2007/0258934 A1 | 11/2007 | Bui et al. | |
| 2008/0102049 A1 | 5/2008 | McDermott | |
| 2008/0233075 A1 | 9/2008 | Sokolinsky et al. | |
| 2009/0074689 A1* | 3/2009 | Auguste | A61K 8/585 424/59 |
| 2011/0098424 A1 | 4/2011 | Carpentier et al. | |
| 2011/0123650 A1* | 5/2011 | Kimura | A61K 8/31 424/729 |
| 2011/0243864 A1 | 10/2011 | Farcet et al. | |
| 2013/0078209 A1 | 3/2013 | Yu et al. | |
| 2013/0164235 A1 | 6/2013 | Lebre-Lemonnier et al. | |
| 2013/0236407 A1 | 9/2013 | Tong et al. | |
| 2013/0236408 A1 | 9/2013 | Bui et al. | |
| 2013/0236409 A1 | 9/2013 | Bui et al. | |
| 2014/0004073 A1 | 1/2014 | Yu et al. | |
| 2015/0272853 A1* | 10/2015 | Kishina | A61K 8/60 424/78.18 |
| 2015/0366789 A1* | 12/2015 | Mei | A61Q 19/02 424/774 |
| 2018/0015023 A1 | 1/2018 | Bernard et al. | |

FOREIGN PATENT DOCUMENTS

| | | | |
|---|---|---|---|
| DE | 19755649 | A1 | 6/1999 |
| DE | 19855649 | A1 | 6/2000 |
| DE | 10162844 | A1 | 7/2003 |
| EP | 0669323 | A1 | 8/1995 |
| EP | 0832642 | A2 | 4/1998 |
| EP | 0893119 | A1 | 1/1999 |
| EP | 0967200 | A1 | 12/1999 |
| EP | 1008586 | A1 | 6/2000 |
| EP | 1027883 | A2 | 8/2000 |
| EP | 1133980 | A2 | 9/2001 |
| EP | 1133981 | A2 | 9/2001 |
| EP | 1300137 | A2 | 4/2003 |
| FR | 2679771 | A1 | 2/1993 |
| FR | 2863493 | A1 | 6/2005 |
| FR | 2887446 | A1 | 12/2006 |
| FR | 2951641 | A1 | 4/2011 |
| GB | 2303549 | A | 2/1997 |
| WO | 93/04665 | A1 | 3/1993 |
| WO | 01/32737 | A1 | 5/2001 |
| WO | 03/042221 | A1 | 5/2003 |
| WO | 2004/006878 | A1 | 1/2004 |
| WO | 2004/024798 | A1 | 3/2004 |
| WO | 2004/085412 | A2 | 10/2004 |
| WO | 2005/058269 | A1 | 6/2005 |
| WO | 2005/100444 | A1 | 10/2005 |
| WO | 2006/032741 | A1 | 3/2006 |
| WO | 2006/034982 | A1 | 4/2006 |
| WO | 2006/034985 | A1 | 4/2006 |
| WO | 2006/034991 | A1 | 4/2006 |
| WO | 2006/034992 | A1 | 4/2006 |
| WO | 2006/035000 | A1 | 4/2006 |
| WO | 2006/035007 | A1 | 4/2006 |
| WO | 2013/190136 | A2 | 12/2013 |
| WO | 2014/143757 | A1 | 9/2014 |
| WO | 2014/167543 | A1 | 10/2014 |
| WO | 2015/091513 | A1 | 6/2015 |
| WO | 2016/100690 | A1 | 6/2016 |

OTHER PUBLICATIONS

Co-pending U.S. Appl. No. 15/094,259, filed Apr. 8, 2016.
Co-pending U.S. Appl. No. 15/087,066, filed Mar. 31, 2016.
Co-pending International Application No. PCT/US2015/066420, filed Dec. 17, 2015.
Co-pending International Application No. PCT/US2015/066516, filed Dec. 17, 2015.
Co-pending International Application No. PCT/US2015/066510, filed Dec. 17, 2015.
Co-pending International Application No. PCT/US2015/066513, filed Dec. 17, 2015.
Burnett, Draft Report on Nylon, Cosmetic Ingredient Review, Jun. 11, 2012, pp. 1-40.
International Search Report and Written Opinion for PCT/US2015/066420, dated Feb. 26, 2016.
International Search Report and Written Opinion for PCT/US2015/066510, dated Feb. 26, 2016.
International Search Report and Written Opinion for PCT/US2015/066513, dated Feb. 26, 2016.
International Search Report and Written Opinion for PCT/US2015/066516, dated Mar. 3, 2016.
English language Abstract for DE 19726184A1 (Dec. 24, 1998).
International Preliminary Report on Patentability for PCT/US2015/066420, dated Jun. 29, 2017.
International Preliminary Report on Patentability for PCT/US2015/066516, dated Jun. 29, 2017.
International Preliminary Report on Patentability for PCT/US2015/066510, dated Jun. 29, 2017.
International Preliminary Report on Patentability for PCT/US2015/066513, dated Jun. 29, 2017.
Non-Final Office Action for co-pending U.S. Appl. No. 15/087,066, dated Sep. 15, 2017.
Sigma-Aldrich specification sheet for poly(dimethylsiloxane-co-methylhydroslloxane) trimethylsilyl terminated (1 page, accessed Sep. 11, 2017, http://www.sigmaaldrich.com/catalog/product/aldrich/482196?lang=en&region=US).
Final Office Action for copending U.S. Appl. No. 15/094,259, dated Jan. 25, 2018.
Final Office Action for copending U.S. Appl. No. 15/087,066, dated Jan. 22, 2018.
Non-Final Office Action for copending U.S. Appl. No. 15/087,066, dated May 9, 2018.
Non-Final Office Action for copending U.S. Appl. No. 15/396,862, dated Oct. 1, 2018.
International Preliminary Report on Patentability for counterpart Application No. PCT/US2016/069271, dated Jul. 12, 2018.
International Preliminary Report on Patentability for counterpart Application No. PCT/US2016/069278, dated Jul. 12, 2018.
International Preliminary Report on Patentability for counterpart Application No. PCT/US2016/069294, dated Jul. 12, 2018.

(56) References Cited

OTHER PUBLICATIONS

Final Office Action for copending U.S. Appl. No. 15/087,066, dated Oct. 25, 2018.
Extended European Search Report for counterpart Application No. 15871123.4-1114, dated Sep. 12, 2018.

* cited by examiner

SILICONE-WAX DISPERSION COMPOSITIONS FOR REMOVING COSMETIC FILMS

This application claims priority to U.S. Provisional Patent Application No. 62/274,081, filed Dec. 31, 2015.

TECHNICAL FIELD

The disclosure relates to compositions and methods for removing cosmetic films and compositions from keratinous fibers.

BACKGROUND

As a person ages, their skin produces less collagen, which provides skin firmness, and elastin, which supplies skin elasticity and rebound, each year. As a result, the skin becomes thinner and more fragile with age, and wrinkle formation as a result of aging is inevitable. It is common for consumers to wish to improve the appearance of such age-related skin imperfections such as wrinkles, crow's feet, eye bags, and the like. Furthermore, as a person ages, other skin imperfections may appear or become more noticeable. For example, age spots, which are brown or gray sun-induced skin lesions, may appear on sun-exposed skin as a person gets older. Additionally, many consumers wish to improve the appearance of, or hide, other skin imperfections such as acne, scars, enlarged pores, and so on, which may not be related to aging.

While cosmetic formulations such as make-up, foundation, or concealer may improve the appearance of some skin imperfections, there is a desire among consumers for more durable and lasting compositions to reduce the appearance of more significant skin imperfections, such as wrinkles, crow's feet, eye bags, and the like. As such, compositions have been developed that form a durable, lasting film on the skin to tighten the skin and reduce the appearance of such skin imperfections, for example those described in PCT/US2015/66420, PCT/US2015/66516, PCT/US2015/66510, PCT/US2015/66513, and U.S. Provisional Application No. 62/274,078. However, these films cannot be removed easily by cosmetic cleansers containing conventional make-up removers or soap and water.

As such, there is a need for compositions that remove such cosmetic films from keratinous fibers, such as the skin, as well as other traditional make-up formulations such as mascara, foundation, eye shadow, and the like.

SUMMARY

The disclosure relates to compositions and methods for removing cosmetic films and makeup compositions from keratinous fibers.

In various embodiments, the disclosure relates to compositions for removing cosmetic films and makeup compositions from keratinous fibers, said compositions comprising at least one solvent comprising at least one low-viscosity, low-volatility silicone oil, wherein the at least one low-viscosity, low-volatility silicone oil is present in the composition in an amount of at least about 20% by weight, relative to the composition, and wherein the at least one low-viscosity, low-volatility silicone oil has a viscosity of less than about 350 cSt.

In further embodiments, the disclosure relates to methods for removing cosmetic films and makeup compositions from keratinous fibers, said methods comprising applying a composition comprising at least one solvent comprising at least one low-viscosity, low-volatility silicone oil, wherein the at least one low-viscosity, low-volatility silicone oil is present in the composition in an amount of at least about 20% by weight, relative to the composition, and wherein the at least one low-viscosity, low-volatility silicone oil has a viscosity of less than about 350 cSt to said keratinous fibers.

DETAILED DESCRIPTION

In various embodiments, the disclosure relates to compositions and methods for removing cosmetic films and makeup compositions from keratinous fibers, such as the skin. Compositions and methods according to the disclosure provide ease of removing cosmetic films, including lasting, durable skin-tightening films, and makeup compositions, including standard and long-wear makeup, with minimal sensation of oiliness.

Compositions for removing cosmetic films and makeup compositions according to the disclosure may comprise at least one low-viscosity, low-volatility silicone oil, and exemplary formulations may be prepared as biphase compositions, water-in-oil (W/O) emulsions, or solvent-wax dispersions.

As used herein, the term "skin-tightening" means that the film that is applied to the skin has contracted in a manner that skin has a tighter feel to the user, and reduces the visual appearance of wrinkles in the skin.

As used herein, the term "lasting" means that the film is substantially intact in place on the skin for a desired period of time.

As used herein, "durable" means the film will not easily rub off, or will not be removed by sweat, water, makeup, lotions, or the like, such that the film will remain substantially intact until removed by the user.

As used herein, when a composition is "free" of a component it means that the component is not present in any measurable amount by standard means, and when it is "substantially free" it is meant that the component is present in an amount that will not affect or substantially affect the properties of the composition, such as, for example, less than about 5%, less than about 4%, less than about 3%, less than about 2%, less than about 1%, less than about 0.5%, less than about 0.1%, less than about 0.05%, less than about 0.01%, less than about 0.005%, or less than about 0.001%.

Solvent

The remover compositions according to various embodiments of the disclosure comprise a solvent chosen from at least one oil with solvent properties. In various embodiments, the at least one solvent comprises one or more low-viscosity, low-volatility, linear and/or cyclic silicone oils. In certain embodiments, the at least one solvent consists of one or more low-viscosity, low-volatility, linear and/or cyclic silicone oils. In further embodiments, the at least one solvent consists essentially of one or more low-viscosity, low-volatility, linear and/or cyclic silicone oils.

As used herein, a "low-volatility" silicone oil has a non-zero vapor pressure at room temperature (25° C.) and pressure. For example, the vapor pressure may range up to about 1300 Pa, such as from about 0.13 Pa to about 130 Pa, or about 0.13 to about 10.6 Pa.

As used herein, a "low viscosity" silicone oil has a viscosity of less than about 400 cSt at 25° C. For example, according to various embodiments, the at least one silicone oil has a viscosity ranging up to about 350 cSt, such as up to about 300 cSt, up to about 250 cSt, up to about 200 cSt, up to about 150 cSt, up to about 100 cSt, up to about 75 cSt, up to about 50 cSt, up to about 25 cSt, up to about 20 cSt, up to about 15 cSt, up to about 10 cSt, or up to about 5 cSt, at 25° C.

In various embodiments, the low-viscosity, low-volatility linear silicones may be chosen from those of formula I:

$$R_3SiO—(R_2SiO)_n—SiR_3 \quad (I)$$

wherein:

R, which may be identical or different, is chosen from:
- a saturated or unsaturated hydrocarbon-based radical, containing from 1 to 10 carbon atoms, such as from 1 to 6 carbon atoms, optionally substituted with one or more fluorine atoms or with one or more hydroxyl groups, or
- a hydroxyl group, one of the radicals R possibly being a phenyl group, and n is an integer ranging from 0 to 8, such as ranging from 2 to 6 or ranging from 3 to 5.

By way of example, silicones of formula (I) that may be chosen include but are not limited to the following: low-viscosity, low-volatility disiloxanes chosen from hexamethyldisiloxane; 1,3-di-tert-butyl-1,1,3,3-tetramethyldisiloxane; 1,3-dipropyl-1,1,3,3-tetramethyldisiloxane; heptylpentamethyldisiloxane; 1,1,1-triethyl-3,3,3-trimethyldisiloxane; hexaethyldisiloxane; 1,1,3,3-tetramethyl-1,3-bis(2-methylpropyl)disiloxane; pentamethyloctyldisiloxane; 1,1,1-trimethyl-3,3,3-tris(1-methylethyl)disiloxane; 1-butyl-3-ethyl-1,1,3-trimethyl-3-propyldisiloxane; pentamethylpentyldisiloxane; 1-butyl-1,1,3,3-tetramethyl-3-(1-methylethyl)disiloxane; 1,1,3,3-tetramethyl-1,3-bis(1-methylpropyl)disiloxane; 1,1,3-triethyl-1,3,3-tripropyldisiloxane; (3,3-dimethylbutyl)pentamethyldisiloxane; (3-methylbutyl)pentamethyldisiloxane; (3-methylpentyl)pentamethyldisiloxane; 1,1,1-triethyl-3,3-dimethyl-3-propyldisiloxane; 1-(1,1-dimethylethyl)-1,1,3,3,3-pentamethyldisiloxane; 1,1,1-trimethyl-3,3,3-tripropyldisiloxane; 1,3-dimethyl-1,1,3,3-tetrakis(1-methylethyl)disiloxane; 1,1-dibutyl-1,3,3,3-tetramethyldisiloxane; 1,1,3,3-tetramethyl-1,3-bis(1-methylethyl)disiloxane; 1,1,1,3-tetramethyl-3,3-bis(1-methylethyl)disiloxane; 1,1,1,3-tetramethyl-3,3-dipropyldisiloxane; 1,1,3,3-tetramethyl-1,3-bis(3-methylbutyl)disiloxane; butylpentamethyldisiloxane; pentaethylmethyldisiloxane; 1,1,3,3-tetramethyl-1,3-dipentyldisiloxane; 1,3-dimethyl-1,1,3,3-tetrapropyldisiloxane; 1,1,1,3-tetraethyl-3,3-dimethyldisiloxane; 1,1,1-triethyl-3,3,3-tripropyldisiloxane; 1,3-dibutyl-1,1,3,3-tetramethyldisiloxane and hexylpentamethyldisiloxane; low-viscosity, low-volatility trisiloxanes chosen from: octamethyltrisiloxane, 3-pentyl-1,1,1,3,5,5,5-heptamethyltrisiloxane; 1-hexyl-1,1,3,3,5,5,5-heptamethyltrisiloxane; 1,1,1,3,3,5,5-heptamethyl 5-octyltrisiloxane; 1,1,1,3,5,5,5-heptamethyl-3-octyltrisiloxane; 1,1,1,3,5,5,5-heptamethyl-3-hexyltrisiloxane; 1,1,3,3,5,5-hexamethyl-1,5-dipropyltrisiloxane; 3-(1-ethylbutyl)-1,1,1,3,5,5,5-heptamethyltrisiloxane; 1,1,1,3,5,5,5-heptamethyl-3-(1-methylpentyl)trisiloxane; 1,5-diethyl-1,1,3,3,5,5-hexamethyltrisiloxane; 1,1,1,3,5,5,5-heptamethyl-3-(1-methylpropyl)trisiloxane; 3-(1,1-dimethylethyl)-1,1,1,3,5,5,5-heptamethyltrisiloxane; 1,1,1,5,5,5-hexamethyl-3,3-bis(1-methylethyl)trisiloxane; 1,1,1,3,3,5,5-hexamethyl-1,5-bis(1-methylpropyl)trisiloxane; 1,5-bis(1,1-dimethylethyl)-1,1,3,3,5,5-hexamethyltrisiloxane; 3-(3,3-dimethylbutyl)-1,1,1,3,5,5,5-heptamethyltrisiloxane; 1,1,1,3,5,5,5-heptamethyl-3-(3-methylbutyl)trisiloxane; 1,1,1,3,5,5,5-heptamethyl-3-(3-methylpentyl)trisiloxane; 1,1,1,3,5,5,5-heptamethyl-3-(2-methylpropyl)trisiloxane; 1-butyl-1,1,3,5,5,5-heptamethyltrisiloxane; 1,1,1,3,5,5,5-heptamethyl-3-propyltrisiloxane; 3-isohexyl-1,1,1,3,5,5,5-heptamethyltrisiloxane; 1,3,5-triethyl-1,1,3,5,5,5-pentamethyltrisiloxane; 3-butyl-1,1,1,3,5,5,5-heptamethyltrisiloxane; 3-tert-pentyl-1,1,1,3,5,5,5-heptamethyltrisiloxane; 1,1,1,5,5,5-hexamethyl-3,3-dipropyltrisiloxane; 3,3-diethyl-1,1,1,5,5,5-hexamethyltrisiloxane; 1,5-dibutyl-1,1,3,3,5,5-hexamethyltrisiloxane; 1,1,1,5,5,5-hexaethyl-3,3-dimethyltrisiloxane; 3,3-dibutyl-1,1,1,5,5,5-hexamethyltrisiloxane; 3-ethyl-1,1,1,3,5,5,5-heptamethyltrisiloxane; 3-heptyl-1,1,1,3,5,5,5-heptamethyltrisiloxane and 1-ethyl-1,1,3,3,5,5,5-heptamethyltrisiloxane; low-viscosity, low-volatility tetrasiloxanes chosen from: decamethyltetrasiloxane; 1,1,3,3,5,5,7,7-octamethyl-1,7-dipropyltetrasiloxane; 1,1,1,3,3,5,7,7,7-nonamethyl-5-(1-methylethyl)tetrasiloxane; 1-butyl-1,1,3,3,5,5,7,7,7-nonamethyltetrasiloxane; 3,5-diethyl-1,1,1,3,5,7,7,7-octamethyltetrasiloxane; 1,3,5,7-tetraethyl-1,1,3,5,7,7-hexamethyltetrasiloxane; 3,3,5,5-tetraethyl-1,1,1,7,7,7-hexamethyltetrasiloxane; 1,1,1,3,3,5,5,7,7-nonamethyl-7-phenyltetrasiloxane; 3,3-diethyl-1,1,1,5,5,7,7,7-octamethyltetrasiloxane; 1,1,1,3,3,5,7,7,7-nonamethyl-5-phenyltetrasiloxane; low-viscosity, low-volatility pentasiloxanes chosen from: dodecamethylpentasiloxane; 1,1,3,3,5,5,7,7,9,9-decamethyl-1,9-dipropylpentasiloxane; 3,3,5,5,7,7-hexaethyl-1,1,1,9,9,9-hexamethylpentasiloxane; 1,1,1,3,3,5,7,7,9,9-undecamethyl-5-phenylpentasiloxane; 1-butyl-1,1,3,3,5,5,7,7,9,9-undecamethylpentasiloxane; 3,3-diethyl-1,1,1,5,5,7,7,9,9-decamethylpentasiloxane; 1,3,5,7,9-pentaethyl-1,1,3,5,7,9,9-heptamethylpentasiloxane; 3,5,7-triethyl-1,1,1,3,5,7,9,9,9-nonamethylpentasiloxane and 1,1,1-triethyl-3,3,5,5,7,7,9,9,9-nonamethylpentasiloxane; low-viscosity, low-volatility hexasiloxanes chosen from: 1-butyl-1,1,3,3,5,5,7,7,9,9,11,11,11-tridecamethylhexasiloxane; 3,5,7,9-tetraethyl-1,1,1,3,5,7,9,11,11,11-decamethylhexasiloxane and tetradecamethylhexasiloxane; hexadecamethylheptasiloxane; octadecamethyloctasiloxane; eicosamethylnonasiloxane; and mixtures thereof.

By way of non-limiting example, the at least one silicone oil may be chosen from low-viscosity, low-volatility linear polydimethylsiloxanes such as DC 200® Fluid 1 cSt, 1.5 cSt, 5 cSt, 10 cSt and 350 cSt, sold by the company Dow Corning, or the one sold by the company Wacker under the name Wacker Belsil® DM 10.

In further embodiments, the low-viscosity, low-volatility silicones may be chosen from cyclic silicones. For example, the low-viscosity, low-volatility cyclic silicones may be chosen from D4-D6 silicones of formula II:

$$-\!\!\left(\mathrm{Si}\!-\!\mathrm{O}\right)_n\!\!-$$

with CH₃ substituents on Si (top and bottom).

Exemplary and non-limiting low-viscosity, low-volatility cyclic silicones include octamethylcyclotetrasiloxane, sold under the name of "Volatile Silicone 7207" by Union Carbide or "Silbione 70045 V 2" by Rhodia; or decamethylcyclopenta-siloxane, sold under the name "Volatile Silicone 7158" by Union Carbide or "Silbione 70045 V 5" by Rhodia.

The at least one low-viscosity, low-volatility, linear and/or cyclic silicone oil may be present in the remover composition in an amount ranging up to, or at least, about 80%, such as up to about 75%, up to about 70%, up to about 65%, up to about 60%, about 55%, up to about 50%, up to about 45%, up to about 40%, up to about 35%, up to about 30%, up to about 25%, up to about 20%, up to about 15%, or up to about 10% by weight, based on the weight of the remover composition.

In at least certain embodiments, the remover compositions according to the disclosure are free or substantially free of silicone oils that are not low-viscosity, not low-volatility, and/or are non-linear. In at least certain embodiments, the remover compositions are free or substantially free of cyclic silicone compounds and/or silicone crosspolymers with solvent properties.

The at least one solvent according to various embodiments may further comprise at least one additional solvent in addition to the low-viscosity, low-volatility, linear and/or cyclic silicone oil. By way of example, the solvent may further comprise solvents chosen from hydrocarbon-based oils such as $C_8$-$C_{16}$ branched alkanes, for instance $C_8$-$C_{16}$ isoalkanes (also known as isoparaffins), isododecane, isodecane, isohexadecane and for example the oils sold under the trade names Isopar and Permethyl, $C_8$-$C_{16}$ branched esters such as isohexyl neopentanoate, and their mixtures, or liquid paraffin or liquid petroleum jelly, mink oil, turtle oil, soybean oil, perhydrosqualene, sweet almond oil, beauty-leaf oil, palm oil, grapeseed oil, sesame seed oil, corn oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate or diglyceryl triisostearate; higher fatty acids such as myristic acid, palmitic acid, stearic acid, behenic acid, oleic acid, linoleic acid, linolenic acid or isostearic acid; or higher fatty alcohols such as cetanol, stearyl alcohol or oleyl alcohol, linoleyl alcohol or linolenyl alcohol, isostearyl alcohol or octyldodecanol.

These additional solvents may be present in the remover composition in an amount up to about 10%, such as up to about 5%, up to about 4%, up to about 3%, up to about 2%, up to about 1.5%, up to about 1%, or up to about 0.5%, by weight of the remover composition.

However, in certain embodiments, the remover composition is free or substantially free of additional solvents, such as hydrocarbon-based oils, alkanes, esters, and/or higher fatty acids.

Water

The remover compositions may, according to at least certain embodiments, comprise water. For example, the biphase or W/O forms of the compositions described herein comprise water in an amount up to, or at least, about 80%, such as up to about 75%, up to about 70%, up to about 65%, up to about 60%, up to about 55%, up to about 50%, up to about 45%, or up to about 40%, by weight of the composition.

In other embodiments, the remover compositions are anhydrous or substantially anhydrous. For example, the solvent-wax dispersions may be free or substantially free of water.

Wax Component

In at least certain embodiments, such as the solvent-wax dispersions described herein, the remover compositions comprise at least one wax. As used herein, the term "wax" is intended to include lipophilic compounds, solid at room temperature (25° C.), with a reversible solid/liquid change of state, having a melting point of greater than or equal to about 25° C., which may optionally range up to about 120° C. In various embodiments, the waxes have a melting point of greater than about 30° C., such as greater than about 45° C.

The melting point of the wax may be measured using a differential scanning calorimeter (DSC), for example the calorimeter sold under the name DSC 30 by Mettler.

The waxes may, in various exemplary embodiments, be hydrocarbon-based waxes, fluoro waxes and/or silicone waxes, and may be of plant, mineral, animal and/or synthetic origin.

Hydrocarbon-based waxes, for instance beeswax, lanolin wax or Chinese insect wax; rice wax, carnauba wax, candelilla wax, ouricury wax, esparto grass wax, cork fibre wax, sugarcane wax, Japan wax and sumach wax; montan wax, microcrystalline waxes, paraffins and ozokerite, polyethylene waxes, the waxes obtained by Fisher-Tropsch synthesis and waxy copolymers, and also esters thereof, may be chosen.

For example, as waxy copolymers, mention may be made of polymers chosen from silicone/(meth)acrylate copolymers, such as those as described in U.S. Pat. Nos. 5,061,481, 5,219,560, and 5,262,087. Also included are those derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545®, or acrylates/stearyl acrylate/dimethicone acrylates copolymers, such as those commercially available from Shin-Etsu, for example, the product sold under the tradename KP-561®, and acrylates/behenyl acrylate/dimethicone acrylates copolymer, such as those commercially available from Shin-Etsu, for example, the product sold under the tradename KP-562®.

Also useful are waxes obtained by catalytic hydrogenation of animal or plant oils containing linear or branched $C_8$-$C_{32}$ fatty chains. Among these waxes, mention may especially be made of hydrogenated jojoba oil, isomerized jojoba oil such as the trans-isomerized partially hydrogenated jojoba oil manufactured or sold by Desert Whale under the commercial reference ISO-JOJOBA-50®, hydrogenated sunflower oil, hydrogenated castor oil, hydrogenated coconut oil, hydrogenated lanolin oil, bis(1,1,1-trimethylolpropane) tetrastearate sold under the name HEST 2T-4S® by Heterene and bis(1,1,1-trimethylol-propane) tetrabehenate sold under the name HEST 2T-4B® by Heterene.

The wax may also be chosen from silicone waxes and siloxane resin waxes (also known as silsesquioxane resin waxes). Exemplary silicone waxes include alkyl or alkoxy dimethicones containing from 16 to 45 carbon atoms. An exemplary silsesquioxane resin wax is a propylsilsesquioxane wax substituted with alkyl units having from 9-40 carbon atoms, or at least 30 carbon atoms. Propylsilsesquioxane waxes are generally described in WO 2005/100444.

The waxes may, in exemplary embodiments, be present in the remover composition in an amount ranging up to, or at least, about 75%, such as up to about 70%, up to about 65%, up to about 60%, up to about 55%, up to about 50%, up to about 45%, up to about 40%, up to about 35%, or up to about 30%, by weight of the composition.

Additional Components

The remover compositions of the present disclosure may optionally include any additional component typically used in products for removing cosmetic films and makeup compositions, with respect to the particular form of the remover composition chosen. For example, when a W/O emulsion is chosen, a person skilled in the art will know which additional components to select to prepare an emulsion and achieve the desired result of removing a cosmetic film or makeup composition, without adversely affecting the properties of the remover compositions.

For example, such additional components may include preservatives, clarifiers, emulsifiers, surfactants, pH adjusting agents, antioxidants, fragrances, colorants such as soluble dyes and pigments, optical brighteners, electrolytes and stabilizers (e.g. sodium chloride, glycerin), plant extracts, proteins, amino acids, vitamins, glycols, emollients, derivatives of the foregoing, and mixtures thereof. Such components may, in various embodiments, be present in the aqueous phase of the composition, for example in the biphase composition or in the W/O emulsion.

Emulsifiers

Non-limiting examples of emulsifiers include amphoteric, anionic, cationic and nonionic emulsifiers, used alone or as a mixture. For example, emulsifiers may be chosen from sorbitan, glycerol or sugar alkyl esters or ethers; silicone surfactants, for instance dimethicone copolyols, such as the mixture of cyclomethicone and of dimethicone copolyol (sold under the name DC 5225 C by the company Dow Corning), and alkyldimethicone copolyols such as lauryl-methicone copolyol (sold under the name Dow Corning 5200 Formulation Aid by the company Dow Corning); cetyldimethicone copolyol (e.g. the product sold under the name Abil EM 90R by the company Evonik), and the mixture of cetyldimethicone copolyol, of polyglyceryl isostearate (4 mol) and of hexyl laurate (e.g. product sold under the name Abil WE O9 by the company Evonik). One or more co-emulsifiers may also be added thereto, which may be chosen for example from the group comprising polyol alkyl esters.

Exemplary polyoxyalkylenated silicone elastomers useful as emulsifiers include those disclosed in U.S. Pat. Nos. 5,236,986, 5,412,004, 5,837,793 and 5,811,487. For example, emulsifiers may be chosen from those available from Shin Etsu: KSG-16 dimethicone (and) dimethicone/vinyl dimethicone corpsspolymer, KSG-21 (at 27% in active material) (INCI name: Dimethicone/PEG-10 Dimethicone vinyl dimethicone crosspolymer), KSG-20 (at 95% in active material) (INCI name: PEG-10 Dimethicone Crosspolymer), KSG-30, (at 100% in active material) (INCI name: Lauryl PEG-15 Dimethicone vinyl dimethicone crosspolymer), KSG-31 (at 25% in active material) (INCI name: Lauryl PEG-15 Dimethicone vinyl dimethicone crosspolymer), KSG-32, KSG-42, KSG-320 or KSG-30 (at 25% in active material) (INCI name: Lauryl PEG-15 Dimethicone vinyl dimethicone crosspolymer), KSG-33: Lauryl PEG-15 (at 20% in active material) (Dimethicone vinyl dimethicone crosspolymer), KSG-210 (at 25% % in active material) (INCI name: Dimethicone/PEG-10/15 crosspolymer), KSG-310 (lauryl modified polydimethylsiloxane polyoxyethylenated in mineral oil), KSG-330 and KSG-340 (PEG-15/lauryl dimethicone crosspolymer, X-226146 (at 32% % in active material) (INCI name: Dimethicone/PEG-10 Dimethicone vinyl dimethicone crosspolymer); and those available from Dow Corning: DC9010 (at 9% in active material) and DC9011 (at 11% in active material) (INCI name: PEG-12 dimethicone crosspolymer), DC9040 cyclopentasiloxane (and) dimethicone crosspolymer, DC9041 dimethicone (and) dimethicone crosspolymer; and mixtures thereof.

In other embodiments, polyglycerolated silicone elastomers may be chosen as emulsifiers. Examples of such compounds are provided in WO 2004/024798. For example, emulsifiers may be chosen from those available from Shin Etsu: KSG-710 (at 25% in active material, INCI name: dimethicone/polyglycerin-3 crosspolymer); and KSG-820, KSG-830 and KSG-840, all of which are dimethicone/polvaleverin-3 crosspolymer (INCI), but in different diluents, 820 is in isododecane, 830 is in triethyl hexanoin and 840 is in squalene.

Colorants

The cosmetic composition of the invention may optionally include at least one colorant. Suitable colorants include, but are not limited to, pulverulent dyestuffs, liposoluble dyes, water-soluble dyes, and pearling agents.

Exemplary pulverulent dyestuffs may, for instance, be chosen from pigments and nacres. Useful pigments include titanium dioxide, zirconium oxide, zinc oxide, cerium oxide, iron oxide, chromium oxide, manganese violet, ultramarine blue, chromium hydrate, and ferric blue. Non-limiting examples of organic pigments include carbon black, pigments of D&C type, and lakes based on cochineal carmine, barium, strontium, calcium, and aluminum.

Exemplary nacres which may be used include, for example, mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Exemplary liposoluble dyes which may be used include Sudan Red, DC Red 17, DC Green 6, beta-carotene, soybean oil, Sudan Brown, DC Yellow 11, DC Violet 2, DC Orange 5, annatto, and quinolone yellow.

Emollients

By way of example only, emollients may be chosen from polyhydroxy compounds including but not limited to glycerin and glycols such as, for example, propylene glycol, butylene glycol, dipropylene glycol and diethylene glycol, glycol ethers such as monopropylene, dipropylene and tripropylene glycol alkyl($C_1$-$C_4$)ethers, monoethylene, diethylene and triethylene glycol.

Preservatives

Non-limiting examples of useful preservatives include ethanol, polyvinyl alcohol, phenoxyethanol, benzyl alcohol, salicylic acid, sodium benzoate, benzoic acid, caprylyl glycol, methyl paraben, propyl paraben, ethylhexylglycerin, 1,3-propanediol, cholorphensin, methylchloroisothiazolinone, methylisothiazolinone, benzalkonium chloride, polyaminopropyl biguanide, and mixtures thereof. In a particular embodiment, the pH adjusting agent is selected from cholorphensin, methylchloroisothiazolinone, methylisothiazolinone, benzalkonium chloride, polyaminopropyl biguanide, and mixtures thereof.

In various embodiments, the compositions may further include additional multi-functional ingredients, for example chelators, such as disodium EDTA, solvents, such as propanediol, and the like.

When present, the additional components may be present in an amount, individual and/or combined, of up to about 10%, such as up to about 8%, up to about 6%, up to about 5%, up to about 4%, up to about 3%, up to about 2%, up to about 1%, up to about 0.75%, up to about 0.5%, up to about 0.25%, up to about 0.1%, up to about 0.05%, up to about 0.01%, up to about 0.005%, or up to about 0.001%, by weight of the remover composition.

The remover compositions may be in any useful form, for example in the form of a cream, a lotion, a biphase product, a pre-loaded wipe, and the like.

Methods

Methods of removing a cosmetic film or makeup composition from keratinous fibers, such as the skin, eyebrows, or eyelashes, using the compositions according to embodiments of the disclosure, are also disclosed. Methods comprise applying the remover composition to the keratinous fibers having a cosmetic film and/or makeup composition thereon, and removing it.

For example, one method may comprise applying the remover composition to a soft pad or pledget and wiping the composition onto the keratinous fibers that have the cosmetic film or makeup composition to be removed. Further exemplary methods may comprise applying the remover composition directly to the keratinous fibers that have the cosmetic film or makeup composition to be removed, or applying the remover composition to the keratinous fibers that have the cosmetic film or makeup composition to be removed with the user's finger(s) or hand(s). In yet further embodiments, the remover may be pre-loaded in a wipe, etc.

In various embodiments, the remover composition may be removed immediately after application, for example by rubbing or wiping the remover composition off the keratinous fibers, or may be allowed to "rest" on the keratinous fibers for a period of time before it is removed. The resting period may range anywhere from a few seconds to a few minutes or more, for example up to about 2 minutes, up to about 1 minute, up to about 45 seconds, up to about 30 seconds, up to about 20 seconds, up to about 10 seconds, or up to about 5 seconds.

The step of rubbing or wiping the remover composition may be done by any method, such as with the soft pad or pledget with which the composition was applied, or with a separate soft pad or pledget. The step of removing the remover composition may also be done with water, for example with a soft pad or pledget or by rinsing.

Additionally, in the case of the cosmetic films described above, the remover composition has an advantage of removing the film in fewer passes with a pad, and in some instances, the film will peel off in a single piece or a few large pieces. This is advantageous because it is quick and easy and convenient for the user, and the user can be certain that the film is completely removed from the skin. Without wishing to be bound by theory, it is believed that this advantage is related to the lower-viscosity of the silicone oil, which provides lower surface tension and higher skin wettability which facilitates the removal in one piece or a few large pieces.

In at least certain embodiments, the keratinous fibers feel smooth and soft after the removal of the cosmetic film and/or makeup compositions by using the remover compositions described herein.

It to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

It is understood that when an amount of a component is given, it is intended to signify the amount of the active material.

It should be understood that all patents and published patent applications referenced are incorporated herein in their entireties.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

The compositions and methods according to the present disclosure can comprise, consist of, or consist essentially of the elements and limitations described herein, as well as any additional or optional ingredients, components, or limitations described herein or otherwise known in the art.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

EXAMPLES

The following Examples are provided for illustrative purposes only, and are not intended to be limiting.

In each of the following examples, the amounts of components given are in terms of active material (AM).

Cosmetic Skin-Tightening Composition

A composition (Table 1) was prepared that provides a cosmetic skin-tightening film on the skin. The thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The oil dispersion (49% in isododecane) and silica silylate were added into the Kraton/isoparaffin oil solution at the specified ratios in a plastic container, and the solution was mixed with a high speed mixer at 2500 rpm/min for 5 minutes. The final solution was kept at room temperature and sealed to avoid the evaporation of solvents.

TABLE 1

Cosmetic Skin-Tightening Composition

| Component | Amount |
|---|---|
| HYDROGENATED STYRENE/BUTADIENE COPOLYMER (Kraton) OIL DISPERSION | 12.1% |
| SILICA SILYLATE | 3.0% |
| ISODODECANE | 38.3% |
| C8-9 ISOPARAFFIN | 34.5% |
| Total | 100.0% |

A moisturizer was first applied to the skin. After 10 minutes, the composition of Table 1 was applied to the skin and allowed to dry. A cosmetic skin-tightening film was formed on the skin.

Example 1: Comparison of Different Oils in Remover Compositions

Several different choices of oils were evaluated for use in remover compositions. The results of this comparison are seen in Table 2.

The cotton-pad test was performed as follows. Approximately 1-3 hours after the cosmetic skin-tightening film was formed on the skin, 15 drops of the remover composition was applied to the film with a small cotton pad. After 10 seconds, the film edge was rubbed with the cotton pad to remove the film, while the number of passes with the cotton pad was counted until the film was completely removed from the skin.

Table 2 shows that low-viscosity, low-volatility linear silicone oils are effective to remove the film from the skin in one piece, and with the fewest cotton pad passes. Esters and alkanes such as isopropyl isostearate and isohexadecane dissolve the film completely, turning it into a tacky film and rendering the removal inconvenient and long.

Example 2: Comparison of Remover Formulations

Several different remover compositions were formulated and compared with commercial formulations.

For the biphase composition, the water phase and oil phase components were mixed separately and the oil phase was added to the water phase at a ratio of 50:50. For the W/O emulsion, the water phase and oil phase components were mixed separately and the water phase was slowly added to the oil phase under strong agitation to create a W/O emulsion. For the solvent-wax dispersion, the wax was melted then the solvent was added to the melted wax, mixed, reheated to homogenize, and then allowed to cool for the wax to harden.

TABLE 2

Comparison of Different Oils in Remover Compositions

| INCI name | Cyclopenta-siloxane | Dimethicone | Dimethicone | Dimethicone | Dimethicone | Isohexa-decane | Isopropyl isostearate |
|---|---|---|---|---|---|---|---|
| Solvent (oil) Type | Silicone | Silicone | Silicone | Silicone | Silicone | Alkane | Ester |
| Viscosity (cSt) | 4 | 5 | 50 | 100 | 350 | 4 | |
| Surface tension (mN/m) | 18 | 19.7 | 20.8 | 20.9 | 21.1 | 24.63 | 29.8 |
| # of cotton pad passes* | 10 | 12 | 14.7 | 13.3 | 17.7 | 25.7 | 28.0 |
| Film integrity (scale 1-4**)* | 1.0 | 1.0 | 1.7 | 1.0 | 1.3 | 4.0 | 4.0 |

*Average on N = 1-3;
**film integrity grading scale (1-4): (1) one piece (film lifted off); (2) several big pieces; (3) lots of very small pieces; and (4) dissolved on cotton pad, no pieces visible.

TABLE 3

Comparison of Remover Formulations

| | Ex. 3-1 BIPHASE | Ex. 3-2 WAX | Ex. 3-3 WATER-IN-OIL EMULSION | Ex. 3C-1 BIPHASE | Ex. 3C-2 MICELLAR WATER |
|---|---|---|---|---|---|
| WATER | | | 48.95% | 64.20% | 51.90% | 96.47% |
| GLYCERIN | | | 3.00% | | |
| SODIUM CHLORIDE | | | 0.50% | 0.50% | 0.48% | |
| PHENOXYETHANOL | | | 0.35% | 0.50% | | |
| CHLORPHENESIN | | | 0.15% | 0.30% | | |
| POLOXAMER 184 | | | 0.05% | | 0.27% | |
| DISODIUM COCOAMPHODIACETATE | | | | | | 1.10% |
| SODIUM LAURETH-8 SULFATE (and) SODIUM LAURETH SULFATE (and) MAGNESIUM LAURETH-8 SULFATE (and) MAGNESIUM LAURETH SULFATE (and) SODIUM OLETH SULFATE (and) MAGNESIUM OLETH SULFATE | | | | | | 0.45% |
| PROPANEDIOL | | | | 5.00% | | |
| DISODIUM EDTA | | | | 0.10% | | 0.05% |
| SODIUM CITRATE | | | | 0.20% | | |

TABLE 3-continued

Comparison of Remover Formulations

| | Ex. 3-1 BIPHASE | Ex. 3-2 WAX | Ex. 3-3 WATER-IN-OIL EMULSION | Ex. 3C-1 BIPHASE | Ex. 3C-2 MICELLAR WATER |
|---|---|---|---|---|---|
| POTASSIUM PHOSPHATE | | | | 0.05% | 0.10% |
| DIPOTASSIUM PHOSPHATE | | | | 0.16% | 0.30% |
| IMIDAZOLIDINYL UREA | | | | | 0.30% |
| QUATERNIUM-15 (and) BENZALKONIUM CHLORIDE | | | | 0.27% | |
| SODIUM BENZOATE | | | | | 0.03% |
| BENZYL ALCOHOL | | | | 0.12% | |
| METHYLPARABEN | | | | | 0.20% |
| DIMETHICONE (5 cSt) | 48.75% | 50.00% | 20.00% | | |
| CYCLOPENTASILOXANE | | | | 27.84% | |
| ISOHEXADECANE | | | | 18.64% | |
| HEXYLENE GLYCOL | | | | 0.27% | 1.00% |
| ACRYLATES/DIMETHICONE COPOLYMER | | 50.00% | | | |
| ISOPROPYL ISOSTEARATE | 1.25% | | | | |
| GREEN 6 | 0.0002% | | | | |
| PEG10 DIMETHICONE | | | 0.20% | | |
| DIMETHICONE (and) DIMETHICONE/PEG-10/15 CROSSPOLYMER | | | 5.00% | | |
| POLYMETHYLSILSESQUIOXANE | | | 1.00% | | |
| TOTAL | 100.00% | 100.00% | 100.00% | 100.00% | 100.00% |
| # of cotton pad passes | 7 | 12 | 15 | 13 | 19 |
| Film integrity (scale 1-4)* | 2 | 2 | 3 | 3 | 2 |
| Oily feel (scale 1-3)** | 2 | 2 | 1 | 2 | 1 |
| Removal of waterproof mascara | Very easy | Very easy | Very easy | Very easy | Not removable |
| Removal of long wear foundation | Easy | Very easy | Easy | Easy | Not easy |
| Removal of non-waterproof mascara | Very easy | Not easy | Easy | Easy | Easy |
| Removal of classical foundation | Very easy | Very easy | Easy | Very easy | Not easy |

*Same as for Table 2;
**oily feel grading scale (1-3): (1) non-greasy, fresh, pleasant; (2) somewhat greasy; (3) very greasy/oily (like dimethicone 5 cSt alone)

The remover compositions of Ex. 3-1 (biphase), 3-2 (solvent-wax dispersion), and 3-3 (W/O emulsion) were used to remove a cosmetic skin-tightening film, waterproof mascara, long-wear foundation, non-waterproof mascara, and standard foundation. Table 3 demonstrates that Ex. 3-1, 3-2, and 3-3 formulations are useful for removing the cosmetic film and various makeup formulations, and has better results than the comparative formulations.

Example 4: Panel/Sensory Testing

The remover composition of Ex. 3-1 was compared to pure dimethicone (5 cSt) using a panel of 8 panelists, aged 40-60. The skin-tightening composition of Table 1 was applied to each of the panelists' faces on the under-eye areas and crow's feet, and a cosmetic skin-tightening film was formed that minimized the appearance of eye bags and crow's feet.

On one half of each of the panelists' faces, the remover composition of Ex. 3-1 was used to remove the cosmetic film, and on the other half of each panelists' face, pure dimethicone (5 cSt) was used to remove the cosmetic film.

Each of the panelists reported good film removal on both sides of the face, but better sensorial results on the side with the remover composition of Ex. 3-1 compared to the pure dimethicone (5 cSt), as it had a less oily feel.

We claim:
1. A composition for removing cosmetic films and makeup compositions, comprising:
  at least one solvent comprising at least one low-viscosity, low-volatility silicone oil chosen from (a) cyclic silicone oils, and (b) linear silicone oils of formula (I):

$$R_3SiO-(R_2SiO)_n-SiR_3 \quad (I)$$

wherein:
  R, which may be identical or different, is chosen from:
    a saturated or unsaturated hydrocarbon-based radical, containing from 1 to 10 carbon atoms, optionally substituted with one or more fluorine atoms or with one or more hydroxyl groups, or
    a hydroxyl group, one of the radicals R optionally being a phenyl group, and
    n is an integer ranging from 0 to 8;
  wherein the at least one low-viscosity, low-volatility silicone oil is present in the composition in an amount of at least about 20% by weight, relative to the composition, and
  wherein the at least one low-viscosity, low-volatility silicone oil has a viscosity of less than about 350 cSt; and
  at least one wax in an amount of at least about 40% by weight, relative to the composition, wherein the composition is in the form of a solvent-wax dispersion.

2. The composition of claim 1, wherein the at least one low-viscosity, low-volatility silicone is present in an amount of at least about 40% by weight, relative to the composition.

3. A method for removing a cosmetic film or makeup composition from keratinous fibers, said method comprising:
  applying to the keratinous fibers a composition comprising:
    at least one solvent comprising at least one low-viscosity, low-volatility silicone oil chosen from (a) cyclic silicone oils, and (b) linear silicone oils of formula (I):

$$R_3SiO-(R_2SiO)_n-SiR_3 \quad (I)$$

wherein:
R, which may be identical or different, is chosen from:
a saturated or unsaturated hydrocarbon-based radical, containing from 1 to 10 carbon atoms, optionally substituted with one or more fluorine atoms or with one or more hydroxyl groups, or
a hydroxyl group, one of the radicals R optionally being a phenyl group, and
n is an integer ranging from 0 to 8;
wherein the at least one low-viscosity, low-volatility silicone oil is present in the composition in an amount of at least about 20% by weight, relative to the total weight of the composition, and
wherein the at least one low-viscosity, low-volatility silicone oil has a viscosity of less than about 350 cSt, and
at least one wax in an amount of at least about 40% by weight, relative to the composition, wherein the composition is in the form of a solvent-wax dispersion, and
removing the composition from the keratinous fibers.

4. The composition of claim 1, wherein the at least one low-viscosity, low-volatility silicone oil has a viscosity ranging up to about 100 cSt.

5. The composition of claim 1, wherein the at least one low-viscosity, low-volatility silicone oil has a viscosity ranging up to about 50 cSt.

6. The composition of claim 1, wherein the at least one low-viscosity, low-volatility silicone oil has a viscosity ranging up to about 10 cSt.

7. The composition of claim 1, wherein the at least one low-viscosity, low-volatility silicone oil has a viscosity ranging up to about 5 cSt.

8. The composition of claim 1, wherein the at least one low-viscosity, low-volatility silicone oil is chosen from polydimethylsiloxanes.

9. The method of claim 3, wherein the at least one low-viscosity, low-volatility silicone is present in an amount of at least about 40% by weight, relative to the composition.

10. The method of claim 3, wherein the at least one low-viscosity, low-volatility silicone oil has a viscosity ranging up to about 100 cSt.

11. The composition of claim 1, wherein the at least one low-viscosity, low-volatility silicone oil has a viscosity ranging up to about 50 cSt.

12. The method of claim 3, wherein the at least one low-viscosity, low-volatility silicone oil has a viscosity ranging up to about 10 cSt.

13. The method of claim 3, wherein the at least one low-viscosity, low-volatility silicone oil has a viscosity ranging up to about 5 cSt.

14. The method of claim 3, wherein the at least one low-viscosity, low-volatility silicone oil is chosen from polydimethylsiloxanes.

* * * * *

UNITED STATES PATENT AND TRADEMARK OFFICE
CERTIFICATE OF CORRECTION

PATENT NO. : 10,292,922 B2  
APPLICATION NO. : 15/087115  
DATED : May 21, 2019  
INVENTOR(S) : Anne-Laure Suzanne Bernard et al.

Page 1 of 1

It is certified that error appears in the above-identified patent and that said Letters Patent is hereby corrected as shown below:

On the Title Page

Item (54), delete "SILICON WAX DISPERSION". The title should read as -- COMPOSITIONS FOR REMOVING COSMETIC FILMS --

Signed and Sealed this  
Second Day of July, 2019

Andrei Iancu  
*Director of the United States Patent and Trademark Office*